United States Patent [19]

Lowitz

[11] Patent Number: 4,707,652
[45] Date of Patent: Nov. 17, 1987

[54] IMPURITY DETECTOR MEASURING PARALLEL POLARIZED SCATTERED ELECTROMAGNETIC RADIATION

[75] Inventor: David A. Lowitz, Richmond, Va.

[73] Assignee: Philip Morris Incorporated, New York, N.Y.

[21] Appl. No.: 793,640

[22] Filed: Oct. 31, 1985

Related U.S. Application Data

[63] Continuation-in-part of Ser. No. 556,736, Nov. 30, 1983, abandoned.

[51] Int. Cl.$^4$ .................................... G01R 27/04
[52] U.S. Cl. ..................... 324/58.5 B; 324/58.5 R; 250/225
[58] Field of Search ............ 324/58.5 B, 58.5 A, 324/58 B, 58 A, 58.5 R, 58 R; 209/535, 536; 250/575, 225

[56] References Cited

U.S. PATENT DOCUMENTS

| | | | |
|---|---|---|---|
| Re. 23,368 | 5/1951 | Grob et al. | 175/183 |
| 2,481,993 | 9/1949 | Fuss | 175/320 |
| 2,576,772 | 11/1951 | Bernet et al. | 175/183 |
| 2,649,538 | 8/1953 | Marlowe et al. | 250/2 |
| 2,660,718 | 11/1953 | Summerhayes, Jr. et al. | 340/258 |
| 2,729,214 | 1/1956 | Broekhuysen et al. | 131/21 |
| 2,922,884 | 1/1960 | Fearnside | 250/71 |
| 3,289,202 | 11/1966 | Preti | 343/5 |
| 3,314,066 | 4/1967 | Schwartz et al. | 343/5 |
| 3,360,721 | 12/1969 | Pullman | 324/58.5 |
| 3,549,986 | 12/1970 | Prine | 324/58.5 |
| 3,557,374 | 1/1971 | Schmermund | 250/207 |
| 3,557,375 | 1/1971 | Schmermund | 250/213 |
| 3,640,626 | 2/1972 | Liskowitz | 250/225 X |
| 3,664,351 | 5/1972 | Russell | 131/110 |
| 3,691,557 | 9/1972 | Constant | 343/6.5 SS |
| 3,729,636 | 4/1973 | Merker | 250/223 R |
| 3,783,373 | 1/1974 | Jawor | 324/58.5 A |
| 3,818,223 | 6/1974 | Gibson et al. | 250/223 |
| 3,854,587 | 12/1974 | McLoughlin et al. | 209/111.7 |
| 3,862,408 | 1/1975 | Bolt | 235/183 |
| 3,940,696 | 2/1976 | Nagy | 325/141 |
| 4,027,303 | 5/1977 | Neuwirth et al. | 340/258 D |
| 4,274,048 | 6/1981 | Tricoles et al. | 324/58 R |
| 4,289,020 | 9/1981 | Paap | 73/61.1 R |
| 4,326,542 | 4/1982 | Laszlo et al. | 131/280 |
| 4,350,170 | 9/1982 | Baier | 131/84 R |

OTHER PUBLICATIONS

Farone, William A., "Electromagnetic Scattering from a Long Dielectric Circular Cylinder at Perpendicular Incidence," Thesis for Master of Science in Chemistry submitted to Clarkson College of Technology, Dept. of Chemistry, 1963.
Farone, William A., "Light Scattering from Cylindrical Obstacles at Normal Incidence," Thesis for Doctor of Philosophy submitted to Clarkson College of Technology, Dept. of Chemistry, 1965.
Summerhill, S., Microwaves as an Industrial Tool, 2/1969, pp. 79–81.
Stolyhwo, A., et al. "Use of Light Scattering as a Detector Principle in Liquid Chromatography," *Journal of Chromatography*, Aug. 10, 1983.

*Primary Examiner*—Reinhard J. Eisenzopf
*Assistant Examiner*—Jack B. Harvey
*Attorney, Agent, or Firm*—Jeffrey H. Ingerman

[57] ABSTRACT

An impurity detector using scattered electromagnetic radiation from a sample of bulk material. It includes a generator of a narrow beam of modulated and linearly polarized electromagnetic radiation directed toward the sample. One or more radiation detectors, the number depending on generator stability and sample characteristics, are responsive to scattered modulated radiation polarized parallel to the polarization of the radiation from the generator. The one or more detectors generate a signal indicating the intensity of such scattered, modulated, and polarized radiation representing a normal sample's angular scattering spectrum. A change in the output of the detector indicates the presence of an impurity in the sample.

29 Claims, 9 Drawing Figures

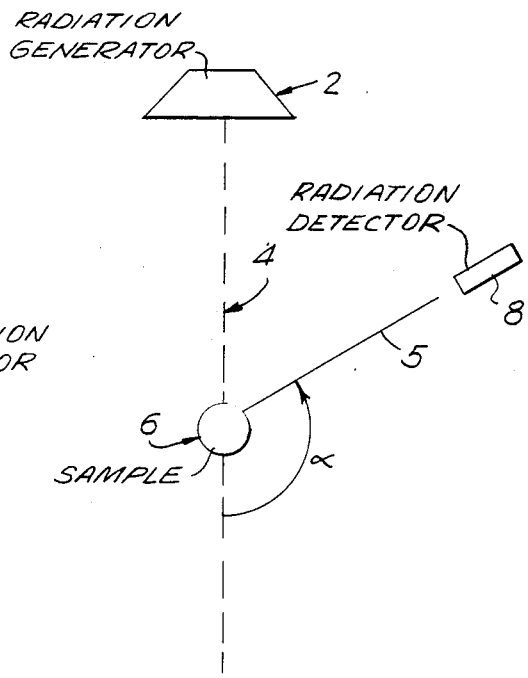
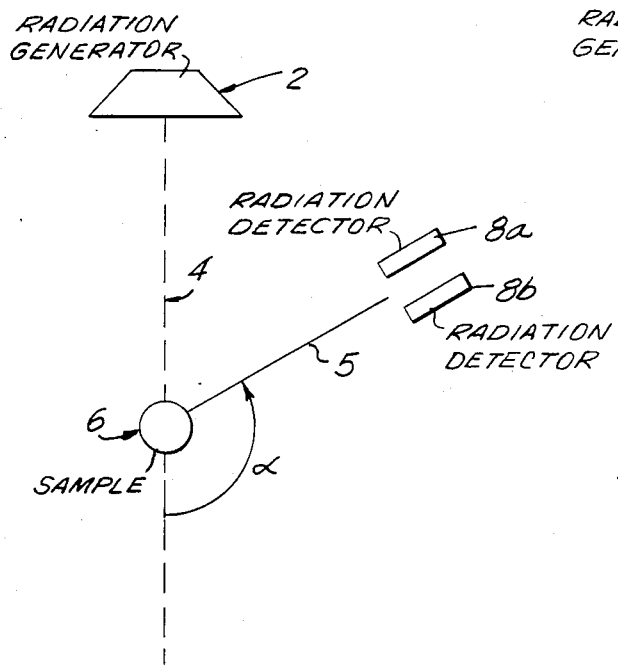
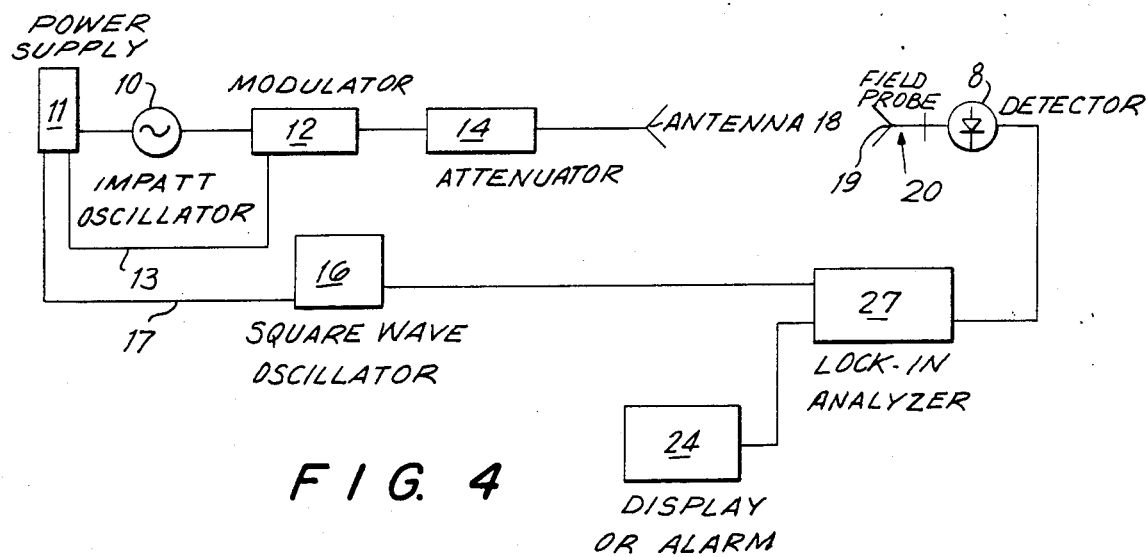

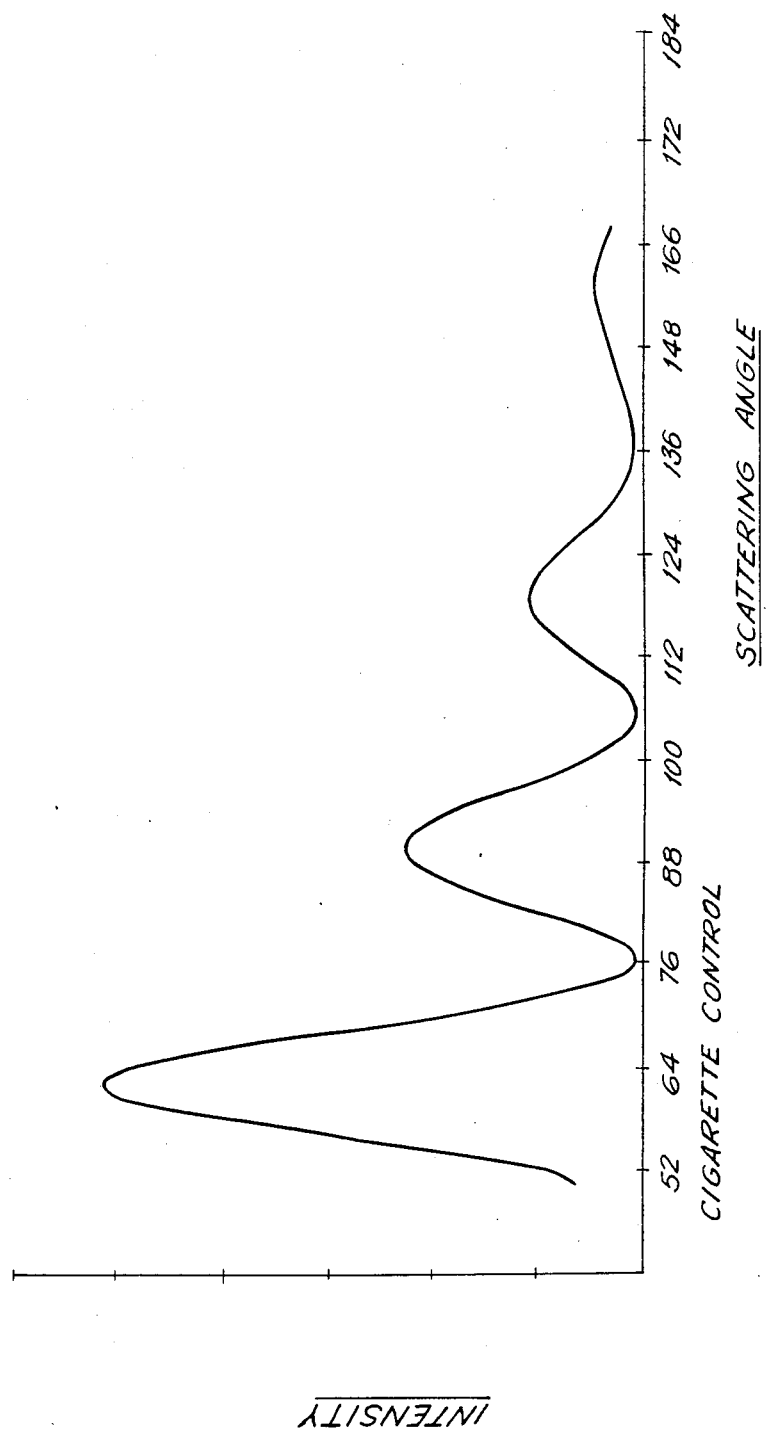

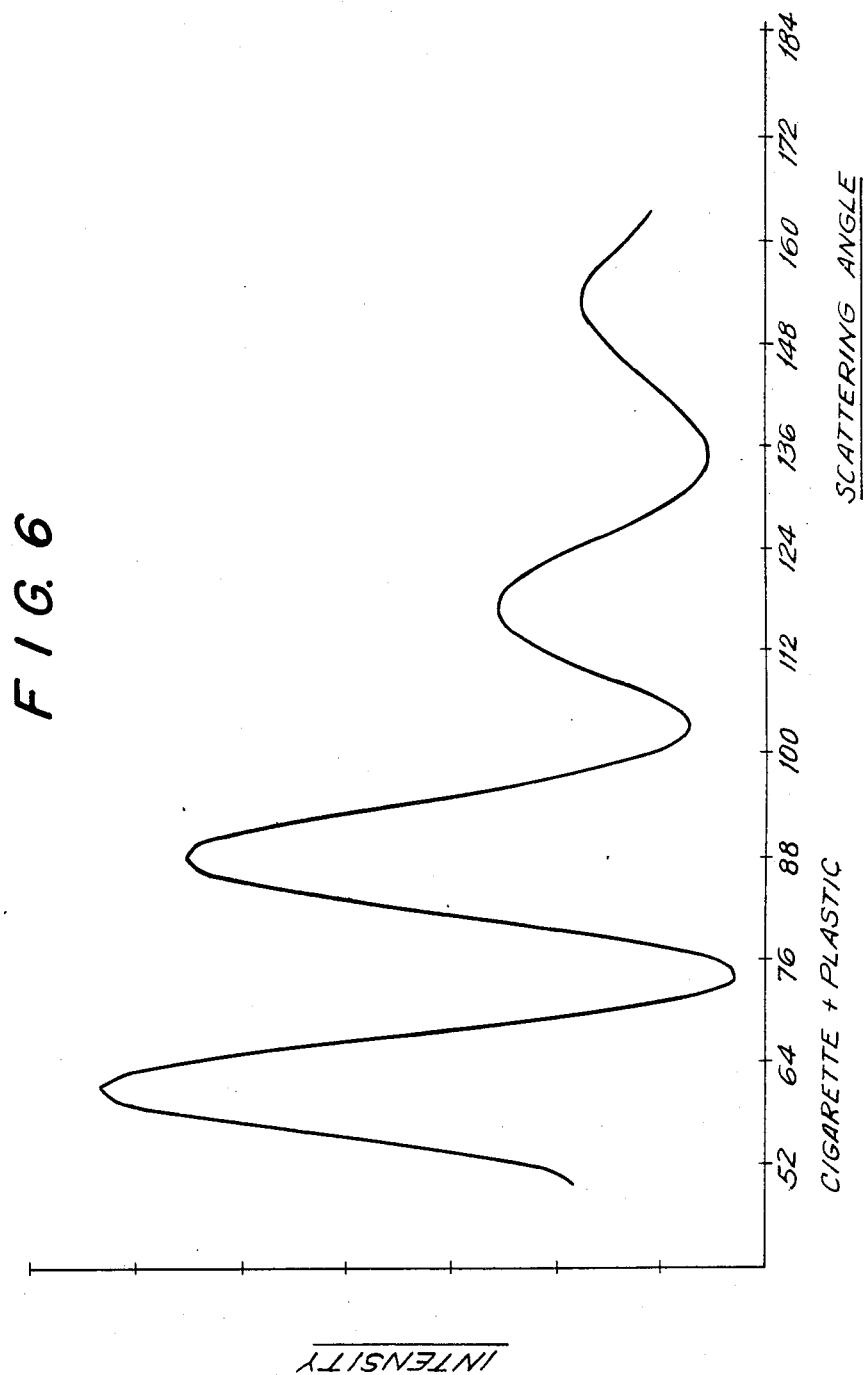

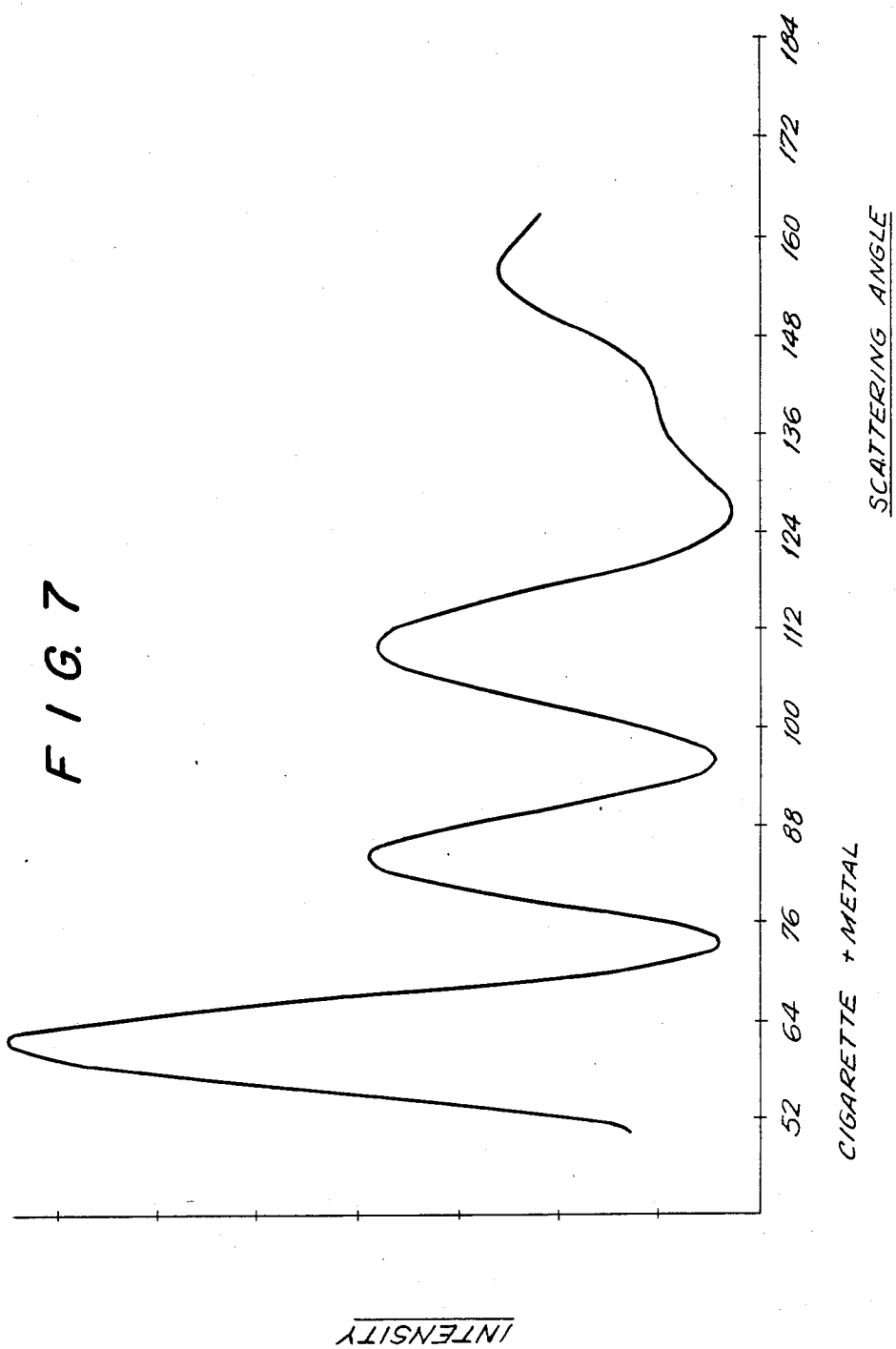

4,707,652

IMPURITY DETECTOR MEASURING PARALLEL POLARIZED SCATTERED ELECTROMAGNETIC RADIATION

CROSS-REFERENCE TO RELATED APPLICATION

This application is a continuation-in-part of copending U.S. patent application Ser. No. 556,736, filed Nov. 30, 1983, now abandoned.

BACKGROUND OF THE INVENTION

This invention relates to impurity detectors. More particularly, this invention relates to impurity detectors using scattered electromagnetic radiation.

Electromagnetic radiation incident on a sample of bulk material undergoes angular scattering due to reflection, interference, and refraction. The magnitude of the scattered radiation depends on the wavelength of the incident radiation, the bulk dielectric constant of the material, and the shape and homogeneity of the sample. Prior to this invention, simple absorption of radiation and scattered cross polarized radiation have been used to analyze samples of bulk material. See, for example, Pullman U.S. Pat. No. 3,360,721, Prine U.S. Pat. No. 3,549,986, and Jawor U.S. Pat. No. 3,783,373. It has been found that parallel polarized scattered radiation is particularly suitable for impurity detection in bulk materials having a predetermined size and shape.

SUMMARY OF THE INVENTION

It is an object of the present invention to provide an impurity detector for bulk materials.

It is a further object of the present invention to provide an impurity detector which measures linearly polarized electromagnetic radiation scattered from a sample of bulk material having a predetermined size and shape. Specifically, scattered radiation with the same linear polarization as the radiation incident on the sample is measured.

In accordance with these objects, there is provided an impurity detector having a source of electromagnetic radiation. The source of radiation directs a beam of linearly polarized electromagnetic energy along a predetermined line of incidence towards a sample of bulk material having a predetermined size and shape. A radiation detection means is sensitive to the angular scattering intensity spectrum. The radiation detection means generates an electrical signal indicating the intensity of scattered radiation having the same linear polarization as the incident radiation. When an impurity is present in the sample, the shape and intensity of the scattered radiation angular spectrum changes so that the presence of the impurity can be detected.

BRIEF DESCRIPTION OF THE DRAWINGS

FIG. 1 is a simplified schematic view of the present invention.

FIG. 2 is a modified schematic view of the present invention showing a pair of detectors.

FIG. 4 is a schematic of the electronic components associated with the present invention.

FIG. 5 is a graph showing the intensity of electromagnetic radiation scattered by a cigarette as a function of scattering angle.

FIG. 6 is a graph showing the intensity of electromagnetic radiation scattered by a cigarette contaminated with plastic as a function of scattering angle.

FIG. 7 is a graph showing the intensity of electromagnetic radiation scattered by a cigarette contaminated with metal as a function of scattering angle.

DETAILED DESCRIPTION OF THE INVENTION

Figure 3:
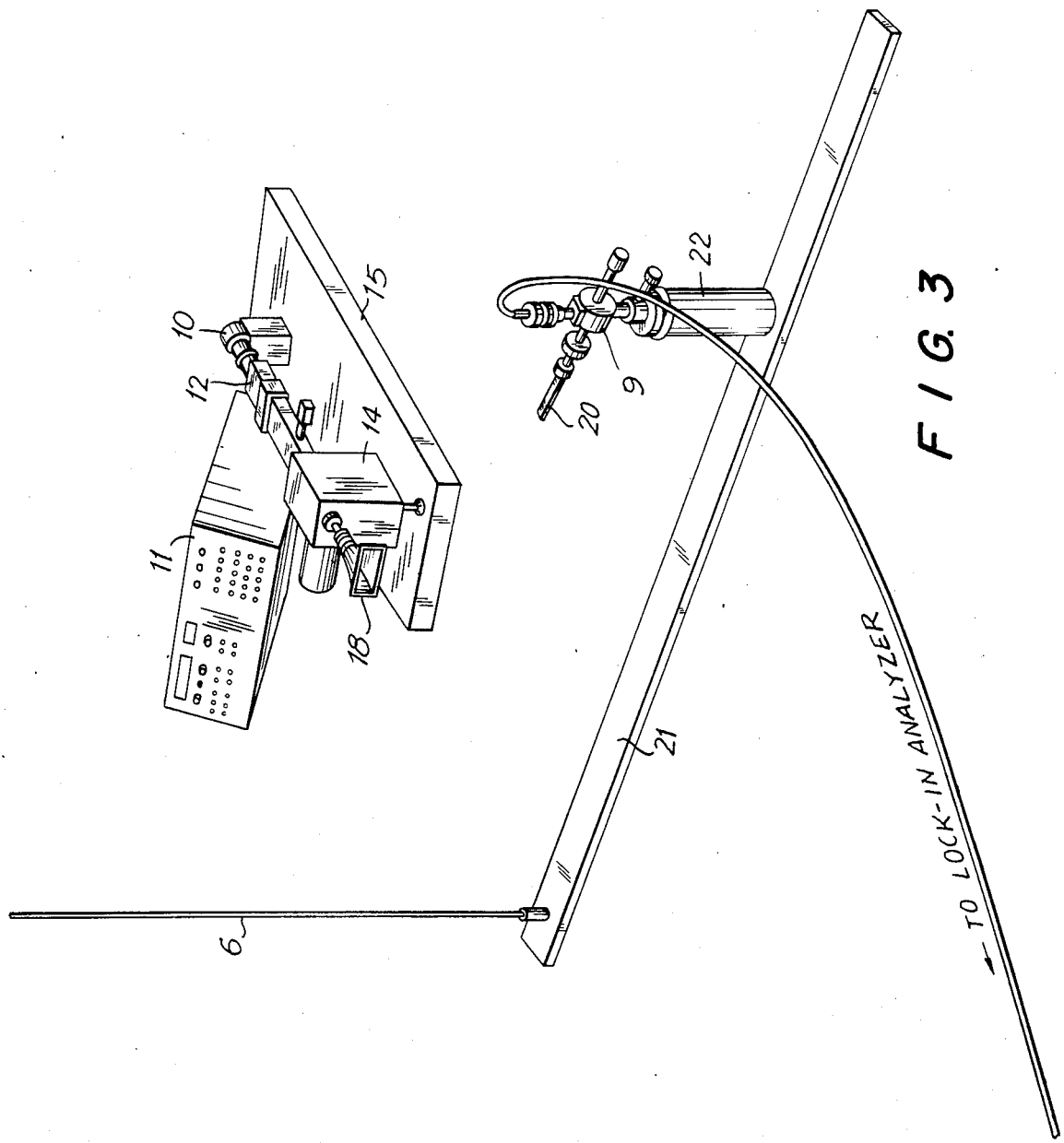
FIG. 3 is a more detailed view of one embodiment of the present invention.

The invention is described by referring to the drawings. Like elements have been assigned like reference numerals throughout the drawings and the written description.

FIG. 1 shows a schematic of one embodiment of the present invention. It includes a radiation generator 2 which directs a narrow beam of linearly polarized electromagnetic radiation along a line of incidence 4 towards a sample 6 of bulk material having predetermined size and shape. For simplicity, only the end of a horn which can be used in a transmitting antenna of the radiation generator is shown in FIG. 1.

The sample can be cylindrical, for example, a tobacco rod such as a cigarette rod traveling in a cigarette make prior to cutting into individual cigarettes. It may also be individual cigarettes or the effluent from a liquid chromatagraph or any bulk material which can take on a fixed size and shape or can be confined to a fixed size and shape container.

The radiation is selected so that it preferably has a frequency which results in a wavelength comparable to the size of the sample to be measured. For objects such as typical cigarettes, the radiation is in the frequency range of about 40 to 90 gigahertz.

A radiation detector 8 is oriented along a line 5 from a scattering angle $\alpha$ with respect to the line of incidence 4. Only a portion of a rectangular waveguide that can serve as a receiving antenna is shown in FIG. 1. Preferably, a horn is used with the waveguide, as described below. The detector detects radiation polarized parallel to the polarization of the radiation incident on the sample and scattered along line 5 by the sample. It converts the scattered polarized radiation into an electrical signal indicating the intensity of such scattered polarized radiation.

A rectangular waveguide feeds electromagnetic energy to the horn in the transmitting antenna. A rectangular waveguide is, in one embodiment, used as a receiving antenna, but, in preferred embodiments, a horn is used in the receiving antenna and a rectangular waveguide conducts radiation from the horn to a sensing element in the detector. In all cases, the horn and rectangular waveguides in the radiation generator and radiation detector have their polarization axes oriented in the same direction so that the radiation generator emits a narrow beam of radiation polarized in a predetermined direction and the radiation detector is sensitive to scattered radiation polarized in that direction.

The distances between the generator and the sample and between the sample and the detector are selected such that the intensity of scattered radiation is compatible with the sensitivity of the detector and its associated circuitry.

The intensity spectrum of the scattered radiation varies between localized maxima and minima as a function of scattering angle (see FIGS. 5 through 7). The scattering angles can be chosen such that typical, expected impurities in the sample produce changes in the output of the detector that can be observed or displayed. Such scattering angles potentially can be at a localized maximum, a localized minimum, or between a maximum and a minimum. When a sample of the bulk material having an impurity is placed in position to receive incident electromagnetic energy, the angular intensity spectrum of scattered radiation changes as compared with the angular intensity spectrum of scattered radiation from an uncontaminated sample. In other words, the intensity of scattered radiation changes at one or more scattering angles when an impurity is introduced into the sample and thus the shape of the angular scattering intensity curve changes. In response to any such change in intensity, the electrical output of a detector at the location of that change also changes. It has been found that, with some samples of bulk materials such as cigarettes and tobacco rods, the scattering angle $\alpha$ should be chosen such that the intensity of scattered radiation from an uncontaminated sample of the bulk material is near, but not at, the maximum of a scattering peak on a sloping portion of the scattered intensity curve. Because the detector is located on a sloping portion of a scattering peak, a small change in position of the localized maximum due to the impurity produces a large change in detector output, even if the height of the scattering peak does not change. This change in electrical output can be displayed in any well-known manner, for example, on an oscilloscope screen, an X-Y recorder, or a digital or analog voltmeter or the change can actuate an audible or visible alarm. Any well-known display or alarm circuitry compatible with the output of the radiation detector is suitable.

Small changes in the effective bulk dielectric constant of the material due to the presence of an impurity produce easily detected shifts in the amplitude and position of the scattering peaks. Thus, inspection of radiation angularly scattered from the material provides a sensitive detector of impurities.

If the radiation generator is highly stable and if the angular scattering spectrum is adequately structured, one radiation detector may provide an adequate representation of the effect of an impurity on the scattering spectrum. Otherwise, more detectors may be necessary, as described below.

FIG. 2 shows a more sensitive indicator of changes in the sample than the indicator shown in FIG. 1 FIG.2 shows a pair of detectors 8a and 8b positioned close together to measure the magnitude of different portions of the same scattering peak. More than two detectors may be used to monitor more than one scattering peak, in order to better avoid sensing changes in the angular scattering spectrum caused by changes in the incident radiation as opposed to sensing changes used by the presence of impurities. Preferably, the two detectors are placed equidistantly on opposite sides of a scattering peak. The electrical output of each detector can be fed to any well-known difference circuit which generates a signal proportional to the difference between the electrical outputs and thus the difference between magnitudes of scattered radiation sensed by the detectors. Alternatively, the electrical output can be fed to a circuit which develops a signal proportional to the ratio of the two detector outputs. These difference and ratio circuits can be any of the many well-known circuits for producing such difference or ratio signals, for example, a dedicated computer, with suitable A/D conversion circuitry, programmed to calculate such differences or ratios.

Single detectors may also be placed at two or more scattering peaks, if desired, the outputs of the detectors being fed to appropriate difference, or ratio circuits as above. Scattering minima may also be monitored by such detectors if appropriate.

In summary, changes in the shape of the angular intensity spectrum of scattered radiation polarized parallel to the polarization of radiation incident on the sample, such changes caused by changes in the effective bulk dielectric constant of the sample, are sensed to detect the presence of an impurity. This is accomplished by locating one or more detectors at selected scattering angles so as to be able to sense such changes in the shape of the intensity spectrum. The type of impurity that can be detected is anything within the sample which changes the effective bulk dielectric constant of the sample beyond a predetermined acceptable deviation. Such changes in effective dielectric constant can be caused, for example, by changes in the chemical composition, packing density, or geometry of the sample as a whole or of small regions within the sample.

FIG. 3 shows in detail the mechanical arrangement of an experimental set up for the present invention. FIG. 4 shows a schematic of the electronic components associated with the generation of the incident radiation and the detection of the angularly scattered radiation in the experimental setup of FIG. 3. FIG. 4 also represents the electronic components used for the embodiment of FIG. 8 described later.

The generator includes a power supply 11 which drives an IMPATT oscillator 10 operating at a desired frequency. For high power applications, an oscillator using a klystron can be used in place of an IMPATT oscillator. The output of the IMPATT oscillator is fed into a modulator 12, preferably a ferrite modulator, through a rectangular waveguide. The modulator is connected to a square wave oscillator 16, operating, for example, at one kilohertz, through the power supply and lines 13 and 17. The modulator square wave modules the output of the IMPATT oscillator at the frequency of the square wave oscillator. The power supply, IMPATT oscillator, and modulator can be a Hughes Full Band Sweep Generator Model No. 47725H-1310. Any arrangement which provides electromagnetic energy at a desired frequency and wavelength modulated at a desired frequency is suitable for the impurity detector.

The output of the modulator is fed to an attenuator 14 through another rectangular waveguide which reduces the output of the modulator to the desired level. The attenuator can be, for example, one of the Hughes 4572xH Series of Millimeter-Wave Direct Reading Attenuators.

The output of the attenuator is connected to a rectangular waveguide and horn 18 forming a transmitting antenna, which in turn generates a narrow modulated beam of polarized radiation at the desired frequency and wavelength towards a cylindrical sample 6 of bulk material. The waveguide and horn can be oriented so that the E-field of the radiation is polarized in the direction of the axis of sample 6, but, for some applications, it may be preferable for the E-field polarization to be normal to the axis of the sample.

As shown in FIG. 3, the microwave generator and associated components can be mounted on a support base 15.

The transmitting horn shown in FIG. 3 is a pyramidal horn with a rectangular cross section. The long side of the horn is parallel to the long side of the rectangular waveguide feeding radiation to the horn. A twisted rectangular waveguide may be used to feed radiation to the horn as long as the long side of the horn is parallel to the long side of the waveguide at the junction of the horn and waveguide. In other embodiments described below, a corrugated conical horn can be used in place of the pyramidal horn.

The sample 6 scatters the incident microwave radiation in all directions at scattering angles with respect to the incident beam. As shown in FIGS. 5 to 7, the intensity of the scattered radiation varies between localized maxima and minima as a function of scattering angle.

A microwave detector 8, preferably a Schottky diode detector, mounted in a housing 9, detects the modulation radiation scattered from the sample. An example of such a detector is a Hughes Model 47315H-1111 tunable broadband detector. A field probe 19 includes a rectangular wave guide 20 pointed at the sample and connected to the input of the detector. The waveguide has its long side parallel to the long sides of the waveguide and horn in the transmitting antenna. The waveguide acts as a receiving antenna and provides improved angular resolution and signal to noise ratio. In other embodiments a horn can be fixed to the input of this waveguide, as shown in FIG. 4. Thus, when a sample of contaminated material, for example, a cigarette contaminated with metal or plastic impurities, replaces an uncontamined sample in the incident beam of radiation, the scattering spectrum changes, as shown in FIGS. 5 to 7, and the intensity of scattered radiation at the selectively placed detector changes thereby changing the output of the detector and indicating the presence of an impurity in the sample.

The detector half wave rectifies the square wave modulated input and removes the carrier. This results in a square wave signal at the output of the detector having a frequency equal to that of the square wave oscillator 16 and having an amplitude related to the intensity of the scattered radiation. The detector thus acts to demodulate the square wave modulated signal. This form of demodulation is exemplary and any well-known square wave demodulator can be used.

The detector 8 and waveguide 20 are mounted on a support 22 which is fixed to an arm 21 rotatable about the stationary sample 6. The arm 21 can be connected to any rotational drive source, for example, an electric motor, so that the angle of the detector with respect to the incident radiation can be adjusted, for example, to a position where an uncontaminated sample produces a desirable scattering peak. Then the position of the detector is fixed.

The output of the detector is fed to the input of a lock-in analyzer 27 which phase matches the output of the detector to the square wave output of oscillator 16. The lock-in analyzer has a band pass filter having a pass band centered about the frequency of the square wave oscillator which acts to convert the signal at the output of the detector into a sinusoidal signal having a frequency equal to that of the square wave oscillator and having a magnitude proportional to the intensity of the scattered radiation. The lock-in analyzer then rectifies and amplifies the sinusoidal signal. The lock-in analyzer can be any well-known circuit which can phase lock the output of the detector to the square wave oscillator. By way of example, the lock-in analyzer can be a Princeton Applied Research Lock-In Analyzer Model 5204. The lock-in analyzer is used to obtain a good signal to noise ratio for the impurity detector by reducing the effects on the scattered radiation signal of spurious signals at the frequency of the radiation.

The output of the lock-in analyzer can be fed to any well-known display or alarm 24 which alerts an observer to an impurity when the amplitude of the signal from the detector changes.

Figure 8:
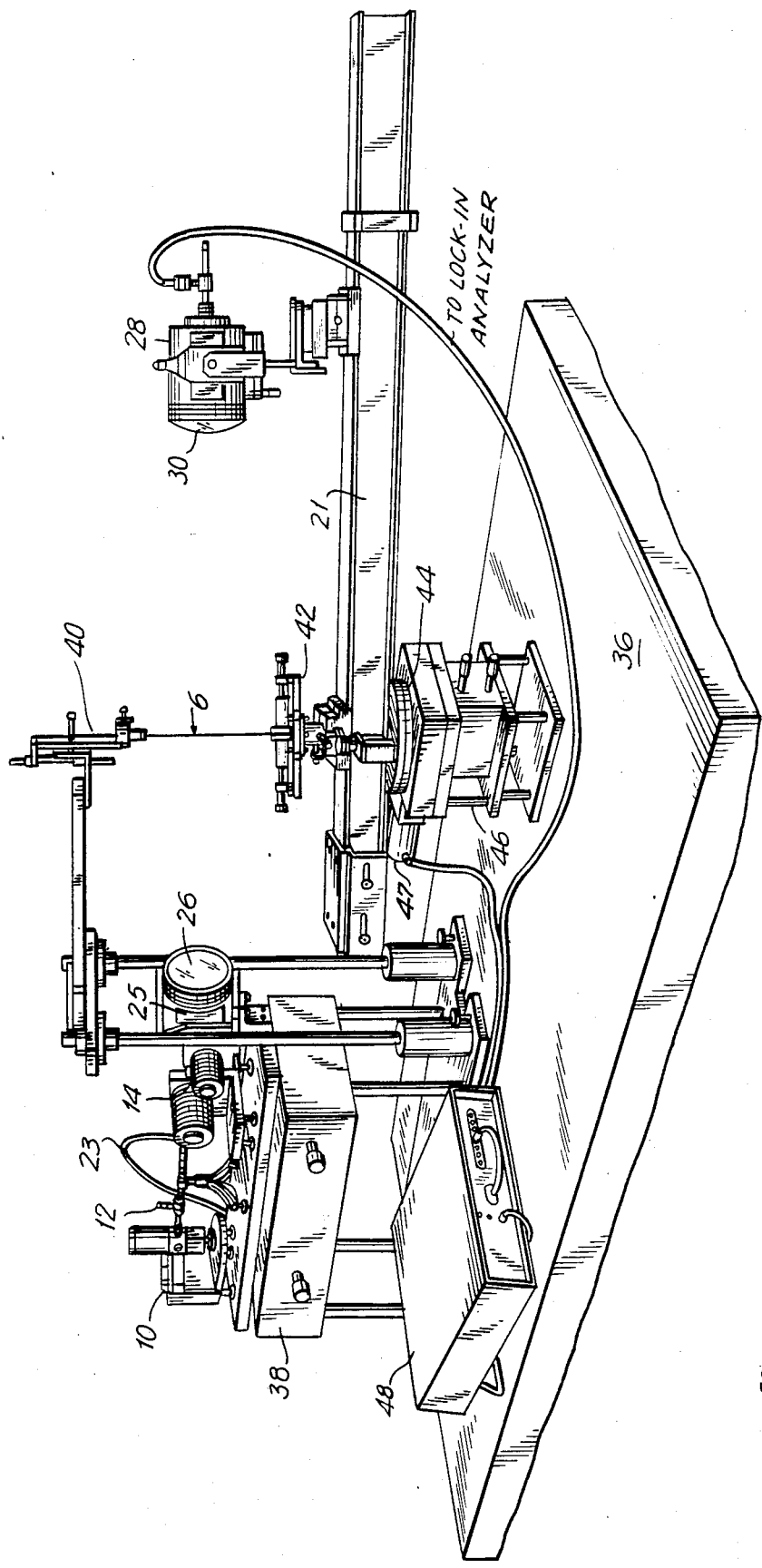
FIG. 8 is a view of an improved impurity detector in accordance with the invention.

FIG. 8 shows an improved embodiment of the invention. This embodiment is similar to the FIG. 3 embodiment with the exception of improved transmitting and receiving antennas for the FIG. 8 embodiment described below. FIG. 8 is described only to the extent necessary to provide an understanding of the differences between FIGS. 3 and 8.

The FIG. 8 embodiment includes an IMPATT oscillator 10 which generates radiation at a desired frequency and wavelength, preferably between 40 to 90 gigahertz. The oscillator is connected to a modulator 12 which is responsive to a relatively low frequency square wave oscillator. The square wave from the square wave oscillator modulates the output of the IMPATT oscillator at the frequency of the square wave oscillator. A signal proportional to the amplitude of the modulated radiation is fed back to amplitude control circuitry in the power supply through coaxial conductor 23 for the purpose of stabilizing the amplitude of the generated radiation. A signal proportional to the frequency of the electromagnetic radiation can be fed back to frequency control circuitry in the power supply to stabilize the frequency of the electromagnetic radiation. The square wave modulated radiation is attenuated by an adjustable attenuator 14. The attenuated radiation is fed to an antenna 25.

Antenna 25 comprises a housing containing a corrugated conical horn (shown in FIG. 9) connected to the attenuator by means of a rectangular waveguide. The long side of the rectangular waveguide, at its junction with the horn, is normal to the E-vector of the polarized field emitted by the horn. The E-vector can be oriented either normal or parallel to the axis of the sample depending on the structure of the TE and TM scattering spectra for the particular sample. A Fresnel lens 26 fitted to the mouth of the antenna housing focuses the microwave radiation onto the sample 6.

The sample 6 scatters the radiation produced by the radiation generator in all directions. One or more radiation detectors are positioned at a predetermined scattering angles with respect to the line of incidence. Those scattering angles are selected in accordance with guidelines given earlier. The radiation detector comprises an antenna 28 having a Fresnel lens 30 for focusing the received radiation. The Fresnel lens is fitted in the mouth of a housing containing a corrugated conical horn like the one described above with waveguide section at the narrower end. The polarization axis of the waveguide is parallel to the polarization axis of the waveguide in the antenna 25. The polarization axes of the transmitting antenna and the receiving antenna are parallel so that the radiation detector is sensitive to scattered radiation polarized in the same direction as the radiation incident on the sample.

Figure 9:
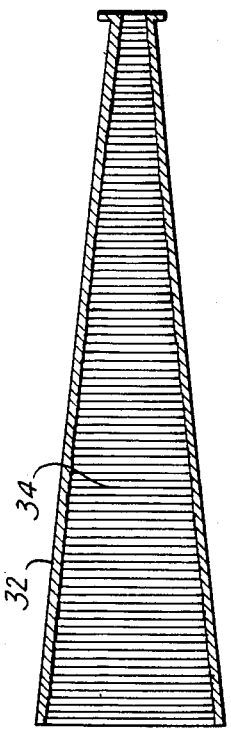
FIG. 9 is a cross section of a horn used in the FIG. 8 impurity detector.

FIG. 9 shows a cross section of a horn 32 suitable for use in the transmitting and receiving antennas. The horn has corrugations 34 on its interior. The Fresnel lenses 26 and 30 are each made of plastic, for example, each lens having a series of concentric corrugations, not shown in FIG. 8. The horn and lens system can be, for example, the GOLA system made by Millitech.

The entire apparatus of FIG. 8 is supported on table 36 which can be any support providing stability to the apparatus. Platform 38 supports the radiation generator at a desired height and levels it with respect to the surface of table 36. Sample supports 40 and 42 hold sample 6 perpendicular to the surface of table 36. Sample support 42 is mounted concentric with the axis of rotation of arm 21 on a turntable 44 supported by base 46.

Arm 21 supports the radiation detector. The angular position of arm 21 is adjustable by an electric motor 47 controlled by motor controller 48. The entire detector can be surrounded by radiation absorbing foam to diminish the effects of stray radiation.

The embodiment of FIG. 8 is a sensitive apparatus which provides a particularly clean signal in the radiation detector which makes it easy to recognize changes in that signal caused by impurities in the sample.

As shown in FIG. 8, the impurity detector is set up for individual cylindrical samples. It can readily be modified so that the sample is effectively a continuous cylinder running between two positions in a manufacturing machine. The turntable is used to position the detector, or detectors, for the particular sample. After positioning the detector, or detectors, at the most desirable positions for a particular sample, the detectors are then fixed at those positions.

What is claimed is:

1. An impurity detector for bulk material comprising:
    a source of electromagnetic radiation for directing a beam of electromagnetic radiation linearly polarized in a predetermined direction along a predetermined line of incidence toward a sample having a predetermined size and shape, said radiation having a predetermined frequency and wavelength; wherein:
    said sample scatters said beam of radiation through reflection, interference, and refraction as a function of scattering angle, the intensity of scattered radiation polarized in a direction parallel to said predetermined direction forming a scattering intensity spectrum varying between localized maxima and minima as a function of scattering angle; said impurity detector further comprising:
    a radiation detection means sensitive to the angular scattering intensity spectrum for generating a signal relating to the intensity of radiation scattered from said sample and polarized only in a direction parallel to said predetermined direction, said signal being characteristic of said angular scattering intensity spectrum, such that said radiation detection means would generate a known intensity signal if said sample were free of impurities, said radiation detection means generating a signal having an intensity different from said known intensity when said sample contains any impurity which changes effective bulk dielectric constant of said sample; and
    means for indicating the presence of an impurity in said sample, said means for indicating being connected to said radiation detection means, wherein said means for indicating responds solely to said differing intensity signal, thereby indicating the presence of an impurity which changes the effective bulk dielectric constant of said sample.

2. The impurity detector of claim 1, wherein said predetermined frequency is in the range of 40 to 90 gigahertz.

3. The impurity detector of claim 1, wherein said sample is cylindrical.

4. The impurity detector of claim 3, wherein said sample is a tobacco rod.

5. The impurity detector of claim 3, wherein said sample is a cigarette rod in a cigarette making machine.

6. The impurity detector of claim 1, wherein said sample is the effluent from a liquid chromatograph.

7. The impurity detector of claim 1, wherein said source of radiation includes an oscillator.

8. The impurity detector of claim 7, wherein said oscillator is connected to a horn through a rectangular waveguide.

9. The impurity detector of claim 1, further comprising a means for modulating the beam of radiation.

10. The impurity detector of claim 9, further comprising a means for demodulating the signal from the radiation detection means.

11. The impurity detector of claim 9, wherein said modulator square wave modulates said beam of radiation.

12. The impurity detector of claim 8, wherein said radiation detection means comprises at least one horn and rectangular waveguide responsive to said scattered radiation.

13. The impurity detector of claim 12, wherein said source of electromagnetic radiation includes a lens for focusing the incident radiation.

14. The impurity detector of claim 13, wherein said radiation detection means includes at least one lens for focusing the scattered radiation.

15. The impurity detector of claim 14, wherein said lenses are Fresnel lenses.

16. The impurity detector of claim 1, wherein said radiation detection means comprises a radiation detector positioned along a line forming a predetermined scattering angle with respect to said line of incidence for generating a signal proportional to said intensity at the location the radiation detector.

17. The impurity detector of claim 16, wherein said scattering angle is selected such that expected impurities in the sample will produce changes in the output of the detector that can be observed.

18. The impurity detector of claim 17, wherein said scattering angle is selected such that the intensity of said scattered radiation is at a localized maximum.

19. The impurity detector of claim 17, wherein said scattering angle is selected such that the intensity of said scattered radiation is at a localized minimum.

20. The impurity detector of claim 17, wherein said scattering angle is selected such that the intensity of said scattered radiation is between a localized maximum and a localized mininum.

21. The impurity detector of claim 1, wherein said radiation detection means comprises:
    a plurality of radiation detectors positioned along lines forming predetermined scattering angles with respect to said line of incidence for generating signals proportional to said intensity of radiation at the locations of those detectors.

22. The impurity detector of claim 21, wherein said plurality of radiation detectors comprises:

a first radiation detector positioned along a line forming a first predetermined scattering angle with respect to said line of incidence; and a second radiation detector positioned along a line forming a second predetermined scattering angle with respect to said line of incidence.

23. The impurity detector of claim 22, wherein said means for indicating comprises a circuit for generating a signal proportional to the difference between the signals generated by said first and second detectors.

24. The impurity detector of claim 22, wherein said means for indicating comprises a circuit for generating a signal proportional to the ratio of the signals generated by said first and second detectors.

25. The impurity detector of claim 22, wherein said first and second detectors are positioned on opposite sides of a localized maximum in the scattering intensity spectrum.

26. The impurity detector of claim 22, wherein said radiation detectors are positioned at scattering angles so as to monitor more than one localized maximum.

27. The impurity detector of claim 12, further comprising an attenuator for attenuating the beam of electromagnetic radiation.

28. The impurity detector of claim 7, where said oscillator is an IMPATT oscillator.

29. The impurity detector of claim 28, wherein said radiation detection means includes at least one Schottky diode detector.

* * * * *